United States Patent [19] [11] 3,937,704
Strandtmann et al. [45] Feb. 10, 1976

[54] 3-(METHYLSULFINYL)CINNOLINONES AND THEIR DERIVATIVES

[75] Inventors: Maximilian von Strandtmann, Rockaway; John Shavel, Jr., Mendham; Sylvester Klutchko, Hackettstown; Marvin Cohen, New Milford, all of N.J.

[73] Assignee: Warner-Lambert Company, Morris Plains, N.J.

[22] Filed: Nov. 15, 1973

[21] Appl. No.: 416,332

Related U.S. Application Data
[62] Division of Ser. No. 190,293, Oct. 18, 1971.

[52] U.S. Cl............................. 260/250 C; 260/578
[51] Int. Cl.²....................................... C07D 237/28
[58] Field of Search............................... 260/250 C

[56] References Cited
UNITED STATES PATENTS
3,669,965   1/1972   White............................ 260/250 C OTHER PUBLICATIONS
Castle, Ed., *Heterocyclic Compounds*, Vol. 28, "Condensed Pyridazines Including Cinnolines and Phthalazines", Wiley—Interscience, N.Y. 1973, p. 87-91, 64-66, 119-120.
Becher et al. I *J. Org. Chem.* 28, 1895 (1963).
Becher et al. II *J. Org. Chem. 28, 1896*.
Becher et al. III *J. Amer. Chem. Soc.* 85, 3410(1963).
Ockenden, et al., *J. Chem. Society* 1953, 3706–3707.

*Primary Examiner*—Donald G. Daus
*Assistant Examiner*—Mark L. Berch
*Attorney, Agent, or Firm*—Albert H. Graddis; Frank S. Chow

[57] ABSTRACT 3-substituted cinnolinones having the following structural formula are disclosed:

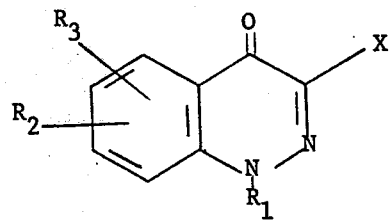

I wherein $R_1$ is hydrogen, lower alkyl, aralkyl or acyl and $R_2$ and $R_3$ are hydrogen, halogen, lower alkoxy or lower alkyl, and X is

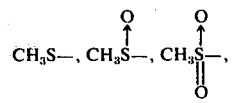

$CH_3COOCH_2S-$, or

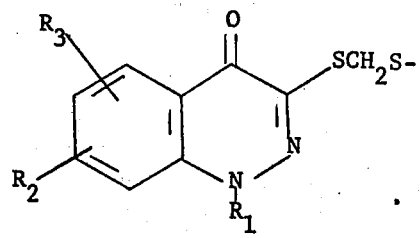

These compounds are useful as immunosuppressants.

1 Claim, No Drawings

3-(METHYLSULFINYL)CINNOLINONES AND THEIR DERIVATIVES

This is a division of application Ser. No. 190,293 filed Oct. 18, 1971.

The present invention relates to 3-substituted cinnolinones having the following structural formula:

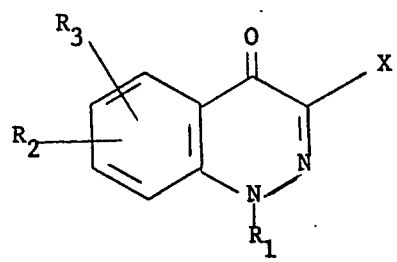

I wherein $R_1$ is H, lower alkyl, aralkyl or acyl and $R_2$ and $R_3$ are hydrogen, halogen, lower alkoxy or lower alkyl, and X is

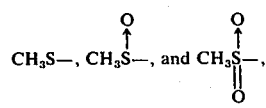

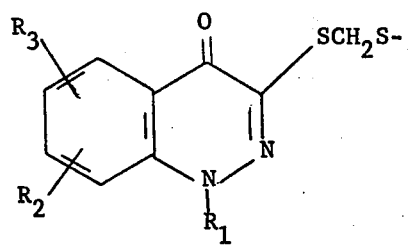

and $CH_3COOCH_2S-$.

In the above definitions for $R_1$, $R_2$ and $R_3$ the term "lower alkyl" and the "alkyl" portion of lower alkoxy is meant to contain from 1 to 6 carbon atoms such as methyl, ethyl, propyl, isopropyl and the like.

The term "aralkyl" is meant to be those groups such as phenyl lower alkyl, typically benzyl, phenethyl and the like.

The term "acyl" includes lower alkanoic acids from 1 to 6 carbons, typically acetic, propionic, and the like.

The compounds of this invention exhibit potent immuno-suppressant activity in a mammalian host. For example, when they are tested in accordance with the procedure described by Jerne, et al., in "Cell-Bound Antibodies," Page 109, Wistar Institute Press, Philadelphia, Pennsylvania (1963), they are capable of inhibiting 90% of the antibody formation at a dose level of 100 mg/kg intraperitoneally in rodents such as rat, guinea pig and the like.

These compounds are indicated as inhibitors of autoimmune responses; for example, in tissue or organ transplants where it is desirable to inhibit the host's immune responses. The dosage level is about 100 mg/kg body weight by intramuscular injection.

In order to use these compounds they are formulated with pharmaceutically acceptable diluents such as water for injection, sesame oil, and the like, by well known methods to the art into dosage forms suitable for intramuscular injection.

The above compounds are prepared in accordance with the following reaction scheme:

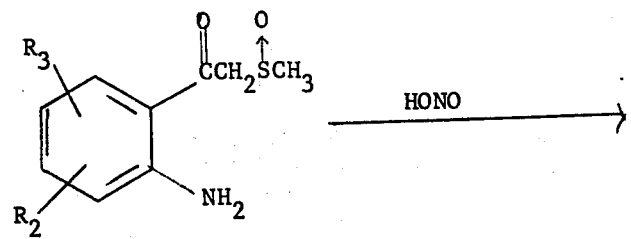

II

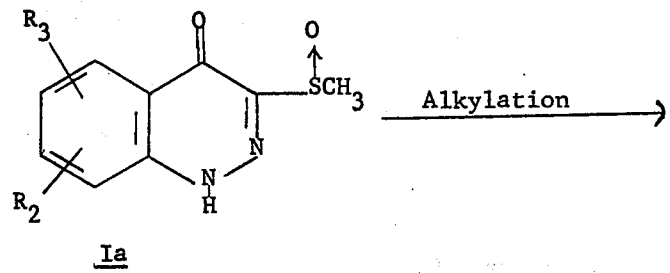

Ia

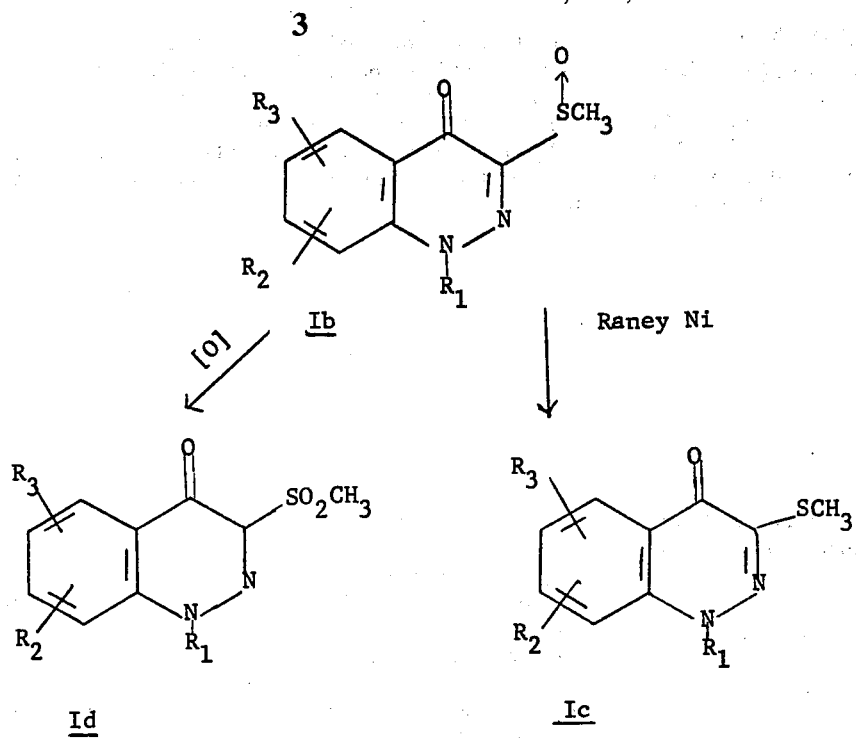

Broadly speaking, starting compounds of Type II are diazotized to yield compounds of Type I*a*. Subsequent alkylation by well known methods yields those compounds of the invention corresponding to structure I*b*.

Oxidation of I*b* with per acids yields the sulfones I*d* and the reduction of I*b* with Raney nickel gives the methylthio derivatives, I*c*.

The compounds of the invention corresponding to structures I*a* and I*b* above undergo Pummerer rearrangement in presence of an acid anhydride to give products of type I*e*.

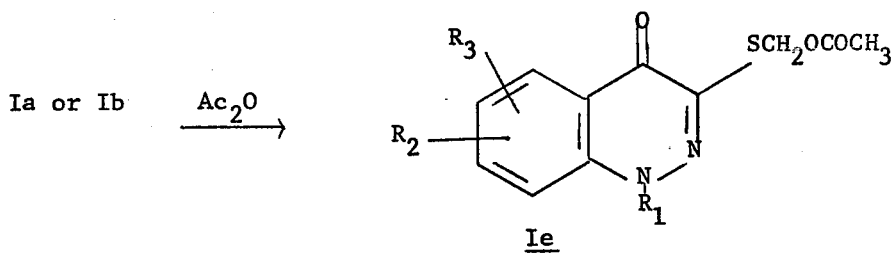

Compounds of Type I*e*, upon refluxing with aqueous mineral acid are converted to compounds of Type I*f*.

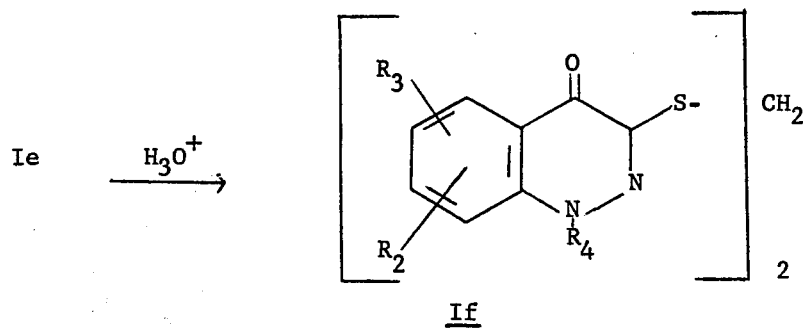

Starting materials of Type II are prepared as follows:

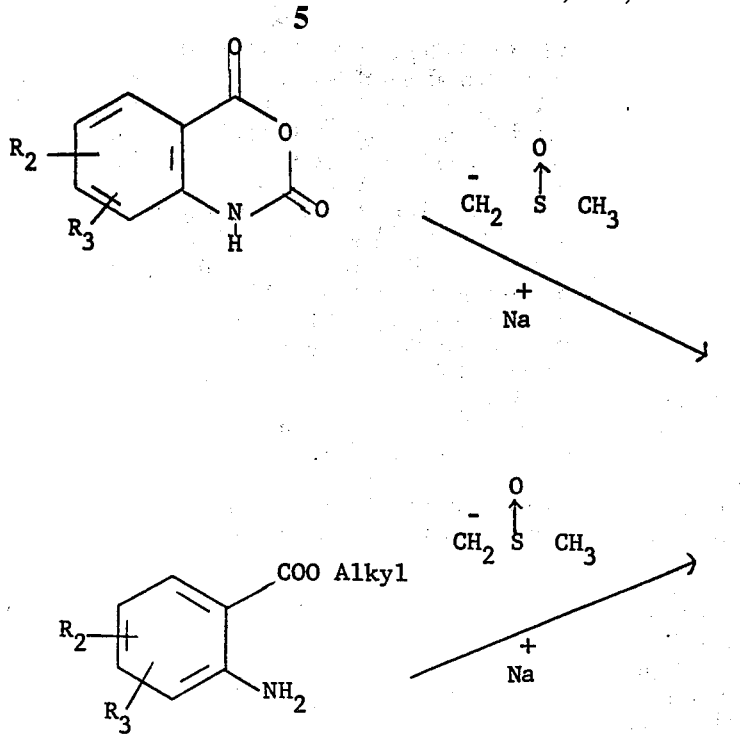

II

The starting materials for Compound II are in turn obtained from the following sources: isatoic anhydrides from Maumee Chemical Co., Toledo, Ohio; dimethylsulfoxide from Crown—Zellerbach Corp., Camas, Washington; NaH from Metal Hydrides, Inc., Beverly, Mass.; ethyl 2-amino-4,5-dimethoxybenzoate was prepared according to Matsmoto, Ber., 11, 135.

In order to further illustrate the practice of this invention, the following examples are included:

Part A — The preparation of starting material of Type II, Examples 1 through 5.

Part B — Preparation of final products, Examples 6 through 22.

PART A

EXAMPLE 1

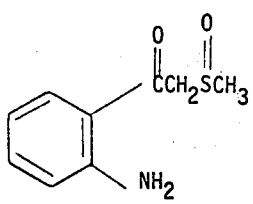

2'-amino-2-(methylsulfinyl)acetophene

Preparation of dimethylsulfoxide anion:

A mixture of 150 ml of dimethylsulfoxide, 350 ml of benzene and 12.7 g (0.3 mole) of 57% sodium hydride-mineral oil dispersion is heated at 70°–75°C for one hour with stirring under nitrogen. The resulting solution is cooled to 30°C.

A quantity of 16.3 g (0.1 mole) of isotoic anhydride is added portion-wise over a period of 5 minutes. The temperature rises to 45°C and is kept at 40°–45°C with mild cooling during the addition. The yellow-green solution is allowed to cool over a period of one-half hour when ether is added to two liters volume. The resulting precipitate is filtered off (hygroscopic), washed well with ether, dried somewhat and dissolved in 100 ml of water. The solution is treated with 15 g (0.25 mole) of glacial acetic acid. Decarboxylation is spontaneous with evolution of carbon dioxide. After several minutes, solid potassium carbonate is added to neutralize and then to saturate the solution. The separated oil is extracted into 250 ml of ethyl acetate and the solution is dried (potassium carbonate) filtered and concentrated to give 10.9 g (55.3%) of a solid melting at 100°–102°C. The crude is recrystallized from ethyl acetate to give pure yellow crystals melting at 101°–103°C.

Anal. Calcd for $C_9H_{11}NO_2S$: C, 54.80; H, 5.62; N, 7.10. Found: C, 55.05; H, 5.71; N, 7.15.

EXAMPLE 2

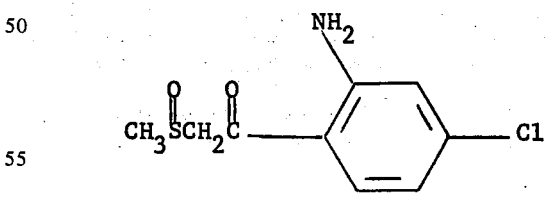

2'-amino-4'-chloro-2-(methylsulfinyl)acetophenone

This compound was prepared by reacting a solution of 13.2 g of NaH (57%) in a mixture of 180 ml. of DMSO and 360 ml. of benzene with 16.8 g of methyl 4-chlororanthranilate (J.A.C.S. 68 1287 (1946) Lutz, et al.) in analogous fashion to 2'-amino-4',5'-dimethoxy-2-(methylsulfinyl)acetophenone. The material was recrystallized from abs. ethanol, m.p. 129°–32°; yield 15 g (72%).

Anal. Calcd for $C_9H_{10}ClNO_2S$: C, 46.65; H, 4.35; S, 13.84. Found: C, 46.56; H, 4.40; S, 13.87.

EXAMPLE 3

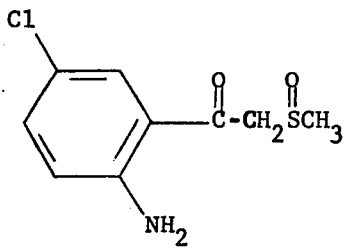

2'-amino-5'-chloro-2-(methylsulfinyl)acetophenone

To a mixture of 600 ml. of benzene and 300 ml. of DMSO was added 22 g. of sodium hydride (55% suspension in mineral oil). The mixture was heated at ca. 75° on a water bath under a stream of nitrogen for 1.5 hr., and the clear solution cooled to 25° in an ice bath. The bath was removed and 29.4 g. of 6-chloroisatoic anhydride was added. The temperature rose to 45°. The solution was stirred for 45 minutes and then diluted to ca. 2500 ml. with anhydrous ether. The precipitate was filtered off, washed with anhydrous ether, and dissolved in 175 ml. of $H_2O$. The solution was treated with 75 ml. of glacial acetic acid, and saturated with $K_2CO_3$. A yellow precipitate formed. This was filtered, washed with cold $H_2O$, and recrystallized from $CH_3CN$, mp. 143°–45°; yield 15 g (43%).

Anal. Calcd for $C_9H_{10}ClNO_2S$: C, 46.65; H, 4.35; N, 6.05; S, 13.85. Found: C, 46.93; H, 4.35; N, 6.30; S, 13.68.

EXAMPLE 4

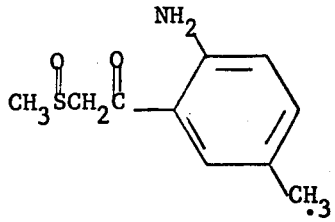

2'-amino-5'-methyl-2-(methylsulfinyl)acetophenone

This compound was prepared by reacting a solution of 44 g of NaH (57%) in a mixture of 600 ml. of DMSO and 1200 ml. of benzene with 50 g of methyl 5-methyl anthranilate (*J. Med. Chem.* 11 500) in analogous fashion to 2'-amino-4',5'-dimethoxy-2-(methylsulfinyl)acetophenone. The material was recrystallized from ethyl acetate with the aid of charcoal, m.p. 145°–47°; yield 30 g (47%).

Anal. Calcd for $C_{10}H_{13}NO_2S$: C, 56.85; H, 6.20; N, 6.63; S, 15.18. Found: C, 56.98; H, 6.21; N, 6.49; S, 15.02.

EXAMPLE 5

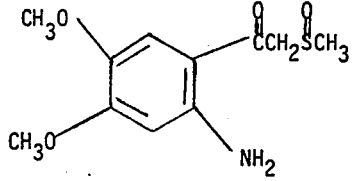

2'-amino-4',5'-dimethoxy-2-(methylsulfinyl)acetophenone

To a mixture of 1 l of benzene and 500 ml of DMSO was added 40 g of NaH (55% in mineral oil). The mixture was heated with stirring at ca. 78° on a water bath under a stream of nitrogen. After 2 hr. hydrogen evolution had ceased, and the solution was clear. The solution was cooled to 25° and 40 g. of ethyl 3,4-dimethoxy anthranilate was added with stirring. The temperature rose to 32°. The mixture was stirred for 45 min. and diluted to 5 l. with anhydrous ether. The precipitated material was filtered, washed with anhydrous ether, and dissolved in 500 ml of $H_2O$. The aqueous solution was adjusted to ca. pH 6 with glacial acetic acid, and the oil that precipitated was extracted with five 100 ml. portions of chloroform. Comb. extracts were dried over $Na_2SO_4$, and concentrated to a heavy oil under reduced pressure. On cooling the oil crystallized. It was recrystallized from abs. EtOH, mp. 162°–64°; yield 34 g (50%).

Anal. Calcd for $C_{11}H_{15}NO_4S$: C, 51.35; H, 5.88; N, 5.44; S, 12.64. Found: C, 51.54; H, 5.97; N, 5.30; S, 12.63.

EXAMPLE 6

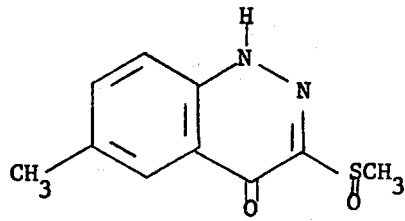

6-methyl-3-(methylsulfinyl)-4(1H)-cinnolinone

This compound was prepared by diazotizing a solution of 18.5 g of 2'-amino-5'-methyl-2-(methylsulfinyl)acetophenone in 500 ml of 1N HCl with 6.3 g of $NaNO_2$ in analogous fashion to 6-chloro-3-(methylsulfinyl)-4(1H)-cinnolinone. The material was recrystallized from DMF, m.p. 265°–67°; yield 15 g (77%).

Anal. Calcd for $C_{10}H_{10}N_2O_2S$: C, 54.04; H, 4.54; N, 12.60; S, 14.43. Found: C, 53.82; H, 4.63; N, 12.60; S, 14.56

PART B

EXAMPLE 7

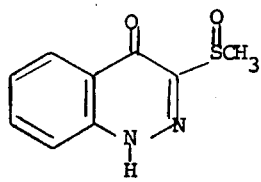

3-(Methylsulfinyl)-4(1H)-cinnolinone

A solution of 5.0 g (0.025 mole) of 2'-amino-2-(methylsulfinyl)-acetophenone, 30 ml (0.03 mole) of cold (15°C) 1N hydrochloric acid and 100 ml of cold water cooled to 5°C. A solution of 2.07 g (0.03 mole) of sodium nitrite in 10 ml of water was added over a period of 3 minutes with stirring, keeping the temperature at 5°C. A deep red color developed as yellow solid separated. The mixture was allowed to warm up to 20°C. After 15 minutes at 20° the product was filtered, washed with water, 2-propanol and then ether. Wt 5.0 g (64%) mp. 266°–269°. Recrystallization from N,N-dimethylformamide gave pure, white crystals melting at 274°–276°C.

Anal. Calcd. for $C_9H_8N_2O_2S$: C, 51.91; H, 3.87; N, 13.45. Found: C, 51.89; H, 3.98; N, 13.41.

EXAMPLE 8

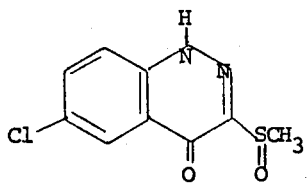

6-Chloro-3-(methylsulfinyl)-4(1H)-cinnolinone 500 ml of 3N HCl was chilled to 0° in an ice-salt bath, and 10 g of 2'-amino-5'-chloro-2-(methylsulfinyl)acetophenone was added. The mixture was stirred until a clear solution was obtained, and a solution of 3.45 g of $NaNO_2$ in 20 ml of $H_2O$ was added with stirring at ca. 0°–3°. The solution became first orange colored, and then a yellow precipitate formed. The ice bath was removed, and the mixture was stirred until room temperature was attained. The precipitate was filtered off, washed with $H_2O$, and recrystallized from dimethylformamide, mp. 267°–72°; yield 5 g (44%).

Anal. Calcd. for $C_9H_7ClN_2O_2S$: C, 44.54; H, 2.91; N, 11.54; S, 13.21. Found: C, 44.62; H, 2.98; N, 11.54; S, 12.96.

EXAMPLE 9

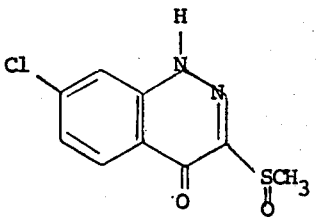

7-Chloro-3-(methylsulfinyl)-4(1H)-cinnolinone

This was prepared in analogous fashion to 6-chloro-3-(methylsulfinyl)-4(1H)-cinnolinone by diazotizing a suspension of 11 g of 2'-amino-4'-chloro-2-(methylsulfinyl) acetophenone in 250 ml of 1N HCl with 3.5 g of $NaNO_2$. The material was recrystallized from dimethyl formamide m.p. 285°–90°; yield 10 g (87%).

Anal. Calcd. for $C_9H_7ClN_2O_2S$: C, 44.54; H, 2.91; N, 11.54. Found: C, 44.38; H, 3.07; N, 11.72.

EXAMPLE 10

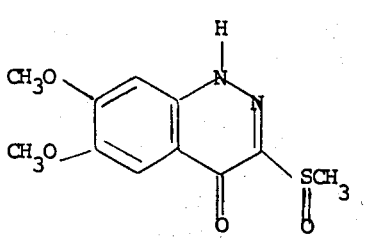

6,7-Dimethoxy-3-(methylsulfinyl)-4(1H)-cinnolinone

A solution of 20 g of 2'-amino-3',4'-dimethoxy-2-(methylsulfinyl) acetophenone in 250 ml of 1N HCl at 0° was treated dropwise with stirring at 0°–5° with a solution of 5.6 g of $NaNO_2$ in 30 ml of $H_2O$. The solution became brown, and a peach colored precipitate formed. The mixture was allowed to warm up to room temperature and the precipitate was filtered, washed with cold $H_2O$, and recrystallized from dimethylformamide, mp. 303°–05°; yield 17 g (81%).

Anal. Calcd. for $C_{11}H_{12}N_2O_4S$: C, 49.25; H, 4.51; N, 10.44; S, 11.95. Found: C, 49.37; H, 4.75; N, 10.56; S, 11.85.

EXAMPLE 11

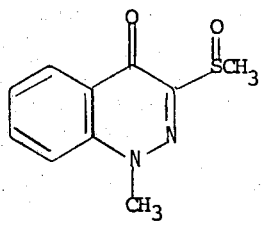

1-Methyl-3-(methylsulfinyl)-4(1H)-cinnolinone

Dimethylsulfate [12.5 g (0.1 mole)] was added gradually to a vigorously stirred solution of 6.5 g (0.0298 mole) of 3-(methylsulfinyl)-4(1H)-cinnolinone in 120 ml of 1N sodium hydroxide solution at 30°C. The temperature rose to 40° as the suspended dimethyl sulfate gradually went into solution over a period of 15 minutes. After an additional one-half hour of stirring, potassium carbonate excess was added to salt-out an oil. The product was extracted into 800 ml of methylene chloride, the solution was dried over $K_2CO_3$, charcoaled, filtered and concentrated. Wt 6.4 g (96.7%) mp. 187°–189°C. Recrystallization from 2-propanol-petroleum ether gave pure material, mp. 189°–191°C.

Anal. Calcd. for $C_{10}H_{10}N_2O_2S$: C, 54.04; H, 4.54; N, 12.60; S, 14.43. Found: C, 54.00; H, 4.55; H, 12.53; S, 14.67.

EXAMPLE 12

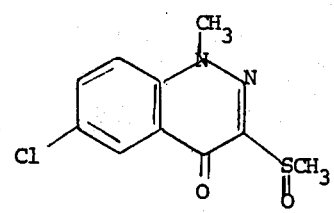

6-Chloro-1-methyl-3-(methylsulfinyl)-4(1H)-cinnolinone

To a solution of 10 g of 6-chloro-3-(methylsulfinyl)-4(1H) cinnolinone in 160 ml of 1N NaOH, was added 15 g of $(CH_3)_2SO_4$ with stirring. The temperature rose to ca 36°, and a thick pasty precipitate formed. After the mixture was allowed to stand for 0.5 hr., it was filtered. The solids were washed with $H_2O$, and recrystallized from abs. ethanol, mp. 231.5°–34.5° yield 6g (60%).

Anal. Calcd. for $C_{10}H_9ClN_2O_2S$: C, 46.79; H, 3.53; N, 10.91; S, 12.49. Found: C, 47.04; H, 3.60; N, 11.20; S, 12.49.

EXAMPLE 13

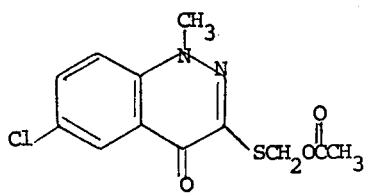

[(6-Chloro-1,4-dihydro-1-methyl-4-oxo-3-cinnolinyl)thio]methanol acetate.

A mixture of 8 g of 6-chloro-1-methyl-3-(methylsulfinyl)-4(1H) cinnolinone and 30 ml of acetic anhydride was refluxed for 2½ hrs. The resulting solution was allowed to stand at room temperature overnight. The crystalline precipitate was filtered off, washed with Skelly B, and recrystallized from $CH_3CN$, mp. 191°–92°; yield 6 g (65%).

Anal. Calcd. for $C_{12}H_{11}ClN_2O_3S$: C, 48.25; H, 3.71; N, 9.38; S, 10.73. Found: C, 48.22; H, 3.67; N, 9.59; S, 10.47.

EXAMPLE 14

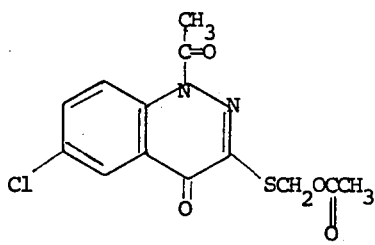

[(1-acetyl-6-chloro-1,4-dihydro-4-oxo-3-cinnolinyl)thio]methanol acetate

A mixture of 12 g of 6-chloro-3-(methylsulfinyl)-4(1H)-cinnolinone and 100 ml of acetic anhydride was refluxed for 3 hours. The solution was chilled, and the crystalline precipitate filtered off, washed with Skelly B, and recrystallized from ethyl acetate, mp. 148°–50°; yield 4 g (24.5%).

Anal. Calcd. for $C_{13}H_{11}ClN_2O_4S$: C, 47.79; H, 3.39; N, 8.57; S, 9.81. Found: C, 48.06; H, 3.54; N, 8.49; S, 10.02.

EXAMPLE 15

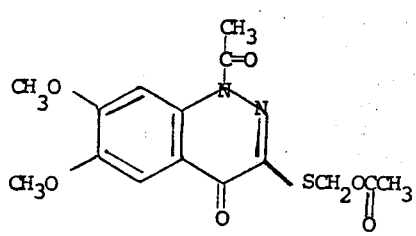

[(1-Acetyl-1,4-dihydro-6,7-dimethoxy-4-oxo-3-cinnolinyl)thio]methanol acetate

A mixture of 13 g of 6,7-dimethoxy-3-(methylsulfinyl)-4(1H) cinnolinone and 500 ml of acetic anhydride was refluxed for 3 hours. The resulting solution was chilled, and the precipitate was filtered off, washed with Skelly B, and recrystallized from $CH_3CN$, mp. 208°–209.5°; yield 11 g (63%).

Anal. Calcd. for $C_{15}H_{16}N_2O_6S$: C, 51.13; H, 4.58; N, 7.95; S, 9.10. Found: C, 51.25; H, 4.65; N, 8.12; S, 9.28.

EXAMPLE 16

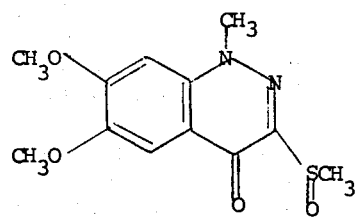

6,7-Dimethoxy-1-methyl-3-(methylsulfinyl)-4(1H)-cinnolinone

A solution of 10 g of 6,7-dimethoxy-3-(methylsulfinyl)-4(1H)-cinnolinone in 148 ml of 1 normal NaOH was treated with 14 g of $(CH_3)_2 SO_4$ with stirring. As the $(CH_3)_2SO_4$ dissolved, the temperature rose to ca. 35° and a pasty precipitate formed. The mixture was stirred for 45 minutes and the precipitate was filtered off, washed with cold $H_2O$ and recrystallized from $CH_3CN$, mp. 262°–64°; yield 6 g (57%).

Anal. Calcd. for $C_{12}H_{14}N_2O_4S$: C, 51.05; H, 5.00; N, 9.92; S, 11.36. Found: C, 51.32; H, 5.24; N, 10.13; S, 11.53.

EXAMPLE 17

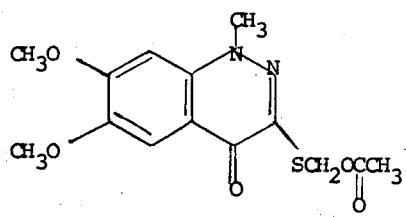

[(1,4-Dihydro-6,7-dimethoxy-1-methyl-4-oxo-3-cinnolinyl)thio]methanol acetate

A mixture of 11 g of 6,7-dimethoxy-1-methyl-3-(methylsulfinyl)-4(1H)-cinnolinone and 100 ml of acetic anhydride was refluxed for 2 hours. The solution was chilled, and the crystalline precipitate was filtered off, washed with Skelly B, and recrystallized from $CH_3CN$, mp. 229°–33°, yield 11 g (87%).

Anal. Calcd. for $C_{14}H_{16}N_2O_5S$: C, 51.84; H, 4.97; N, 8.64; S, 9.89. Found: C, 51.86; H, 5.09; N, 8.41. S, 10.03.

EXAMPLE 18

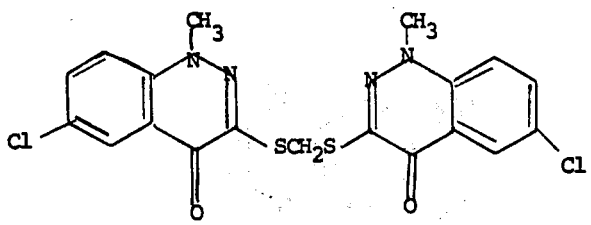

3,3'-Methylenedithiobis(6-chloro-1-methyl-4(1H)-cinnolinone)

A mixture of 10 g of [(6-chloro-1,4-dihydro-1-methyl-4-oxo-3-cinnolinyl)-thio]methanol acetate and 250 ml of 3N HCL was refluxed with stirring for 5 hours. The mixture was then chilled, and the precipitate filtered off washed with cold $H_2O$, and recrystallized from dimethylformamide, mp. 352°–54°; yield 5.5 g (73%).

Anal. Calcd. for $C_{19}H_{14}Cl_2N_4O_2S_2$: C, 49.04; H, 3.03; N, 12.04; S, 13.78. Found: C, 49.23; H, 3.22; N, 12.24; S, 13.60.

EXAMPLE 19

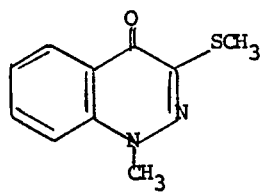

1-Methyl-3-(methylthio)-4(1H)-cinnolinone

A mixture of 0.4 g (0.0018 mole) of 1-methylsulfinyl)-4(1H)-cinnoline, 50 ml of water and 3.5 g of Raney nickel was boiled with stirring for 10 minutes. The cooled reaction mixture was filtered. The Raney nickel was extracted with 50 ml of methylene chloride. The dried ($K_2CO_3$) extract concentrated to give 10 mg (2.7%) of yellow crystals melting at 173°–175°. Recrystallization from benzene-petroleum ether gave pure material, m.p. 175°–177°C.

Anal. Calcd. for $C_{10}H_{10}N_2OS$: C, 58.23; H, 4.89; N, 13.58. Found: C, 58.44; H, 4.90; N, 13.64.

EXAMPLE 20

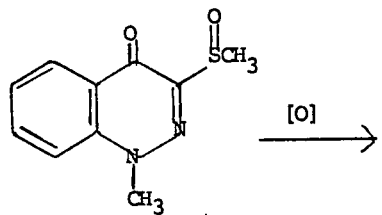

1-Methyl-3-(methylsulfonyl)-4(1H)-cinnolinone

A quantity of 6.16 g (0.027 mole) of 85% m-chloroperbenzoic acid was added to a solution of 6.6 g (0.03 mole) of 1-methyl-3-(methylsulfinyl)-4(1H)-cinnolinone in 100 ml of chloroform. The temperature rose to 45° C. After 5 minutes the solution was brought to reflux for 5 minutes, cooled, mixed with 200 ml of 5% sodium bicarbonate and stirred for 10 minutes. Additional chloroform (300 ml) was added to dissolve the separated product. The organic layer was separated, dried over anhydrous potassium carbonate and concentrated to give 6.7 g (94.4%) of white product melting at 202°–204°. Recrystallization from chloroform-methanol gave pure product melting at 204°–206° C.

Anal. Calcd. for $C_{10}H_{10}N_2O_3S$: C, 50.41; H, 4.23; N, 11.76. Found: C, 50.46; H, 4.30; N, 11.80.

EXAMPLE 21

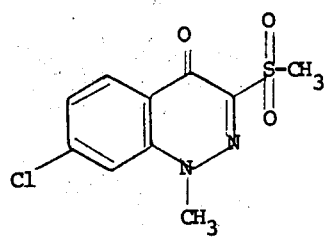

7-Chloro-1-methyl-3-(methylsulfonyl)-4(1H)-cinnolinone

This was prepared by oxidizing a solution of 10 g of 7-chloro-1-methyl-3-(methylsulfinyl)-4(1H)-cinnolinone in 500 ml of $CHCl_3$ with 7.5 g of m-chloroperbenzoic acid in analogous fashion to 1-methyl-3-(methylsulfonyl)-4(1H)-cinnolinone. The material was recrystallized from $CH_3CN$, m.p. 270°–72°; yield 7.5 g (71%).

Anal. Calcd. for $C_{10}H_9ClN_2O_3S$: C, 44.04; H, 3.33; N, 10.27; S, 11.76. Found: C, 44.32; H, 3.22; N, 10.29; S, 12.05.

EXAMPLE 22

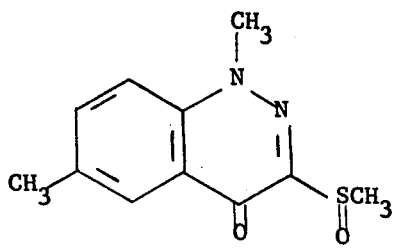

1,6-dimethyl-3-(methylsulfinyl)-4(1H)-cinnolinone

This compound was prepared by reacting a solution of 8 g of 6-methyl-3-methylsulfinyl)-4(1H)-cinnolinone in 145 ml of 1N NaOH with 13.5 g of dimethylsulfate in analogous fashion to 1-methyl-3-(methylsulfinyl)-4(1H)-cinnolinone. The material was recrystallized from ethyl acetate, m.p. 173°–75°; yield 5.5 g (65%).

Anal. Calcd for $C_{11}H_{12}N_2O_2S$: C, 55.91; H, 5.12; W, 11.86; S, 13.57. Found: C, 56.19; H, 5.17; N, 11.97; S, 13.71.

We claim:
1. A process for the production of a compound of formula I:

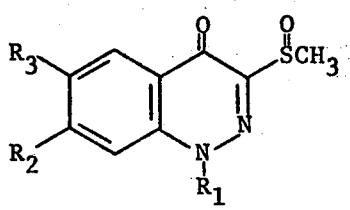

wherein $R_1$ is methyl, and $R_2$ and $R_3$ are hydrogen, chlorine, methyl and methoxy, comprising the steps of:
a. treating compounds of formula II:

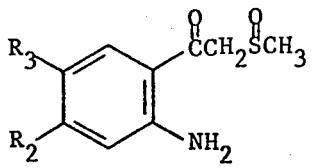

with sodium nitrite and hydrochloric acid to give a compound of formula III:

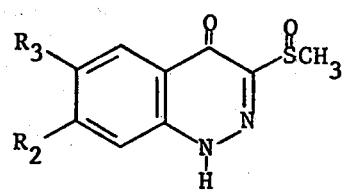

wherein $R_2$ and $R_3$ are as hereinbefore defined;
b. treating compounds of formula III wherein $R_2$ and $R_3$ are as hereinbefore defined with a dialkylsulfate having 1 to 6 carbon atoms in the alkyl residue and an alkali metal hydroxide; and
c. recovering the products of formula I wherein $R_1$, $R_2$ and $R_3$ are as hereinbefore defined.

* * * * *